United States Patent [19]

Neel et al.

[11] Patent Number: 4,983,260
[45] Date of Patent: Jan. 8, 1991

[54] PROCESS FOR CONCENTRATING AQUEOUS ETHYLENE OXIDE SOLUTIONS

[76] Inventors: Henri Neel, 7 Boulevard Francois ler, 76600 Le Havre; Francis DeLannoy, 61, rue Ampére, 69310 Pierre-Benite, both of France

[21] Appl. No.: 333,843

[22] Filed: Apr. 3, 1989

Related U.S. Application Data

[63] Continuation of Ser. No. 631,163, Jul. 16, 1984, abandoned.

[30] Foreign Application Priority Data

Oct. 19, 1983 [FR] France .................... 83 16615

[51] Int. Cl.⁵ .................................... B01D 3/00
[52] U.S. Cl. ......................... 203/14; 55/51; 203/42; 203/87; 203/93; 203/94; 203/96; 203/97; 203/98; 549/538; 549/542; 568/867; 568/868
[58] Field of Search ............ 203/87, 97, 93, 94, 203/96, 42, 14, 98; 202/186, 202, 198; 549/538, 542; 55/51; 568/867, 868

[56] References Cited

U.S. PATENT DOCUMENTS

| | | | |
|---|---|---|---|
| 2,615,901 | 10/1952 | McClellan | 568/867 |
| 3,165,539 | 1/1965 | Lutz | 549/538 |
| 3,745,092 | 0/0000 | Vandewater | 203/42 |
| 3,766,714 | 10/1973 | Cunningham et al. | 55/51 |
| 3,964,980 | 6/1976 | Ozero | 203/96 |
| 4,033,617 | 7/1977 | Cocuzza et al. | 202/198 |
| 4,134,797 | 1/1979 | Ozero | 203/DIG. 19 |
| 4,437,938 | 3/1984 | Bhise et al. | 203/49 |

Primary Examiner—Virginia Manoharan
Attorney, Agent, or Firm—Sigalos, Levine & Montgomery

[57] ABSTRACT

A process for the concentration of ethylene oxide in an impure solution thereof including adding the solution and steam to a distillation column, recovering the gaseous stream therefrom containing ethylene oxide, and progressively condensing the steamed solution in at least two heat exchangers arranged in series, with the absolute pressure of the distillation column and of the exchangers being between about 1.5 and 6 bars and the temperature of the cooling fluid of the last exchanger being between about 5° C. and a maximum temperature 5° C. below the temperature of condensation of pure ethylene oxide at the pressure used.

11 Claims, 1 Drawing Sheet

PROCESS FOR CONCENTRATING AQUEOUS ETHYLENE OXIDE SOLUTIONS

This application is a continuation of application Ser. No. 631,163, filed July 16, 1984, now abandoned.

BACKGROUND OF THE INVENTION

The present invention concerns the manufacture of ethylene oxide. More precisely, the invention concerns a process and apparatus system for concentrating aqueous ethylene oxide solutions, such as, for instance, those solutions obtained by water absorption of ethylene oxide in order to separate it from the reaction mixture of synthesis.

On an industrial scale, ethylene oxide generally is prepared by the oxidation in the gaseous phase of ethylene by oxygen in the presence of a catalyst based on silver. Since the ethylene oxide is very dilute in the gaseous mixture produced from the oxidation reaction, this mixture must subsequently be subjected to various treatments (absorptions, distillations, flash, and the like) in order to obtain pure ethylene oxide (see for instance French Pat. No. 1,343,492, French Pat. No. 2,305,436 and U.S. Pat. No. 3,904,656).

In practice, the isolation of ethylene oxide from the gaseous mixture obtained from the synthesis is carried out in several steps:

(a) Water Absorption: The gaseous mixture is placed in contact with water in a column including several theoretical stages or gas-liquid contact devices. In this matter, an aqueous solution is obtained containing about 2.5% by weight of ethylene oxide, as well as dissolved gases ($CO_2$, $CH_4$, $C_2H_4$, nitrogen, argon, etc.) and other impurities (principally formaldehyde and acetaldehyde);

(b) Desorption: The above aqueous solution is "stripped" in a distillation column, with or without an enrichment section. At the base one obtains an aqueous stream no longer containing ethylene oxide and at the top a mixture of ethylene oxide, steam and dissolved gases and other impurities initially present in the aqueous ethylene oxide solution. This gaseous stream has an ethylene oxide content of about 30 to 60% by weight;

(c) Reabsorption: The preceding gaseous stream is cooled, then placed in contact with water in order to reabsorb the ethylene oxide. The greatest part of the dissolved gases is not reabsorbed in the water and is easily separated in the form of a gas stream. An aqueous ethylene oxide solution is obtained whose concentration is between 5 and 15% by weight; and (d) Distillation: The solution is then distilled in order to obtain pure ethylene oxide.

The energy required in order to separate the two constituents from this solution increases as the ethylene oxide content decreases. Thus, while the gaseous mixture issuing from step (b) contains about 30 to 60% by weight of ethylene oxide, water must be readded in order to reabsorb the ethylene oxide and this step subsequently requires a considerable amount of energy in order to separate this water from the ethylene oxide.

SUMMARY OF THE INVENTION

The present invention overcomes the problems of the prior art and provides a concentrated aqueous solution containing at least 95% by weight of ethylene oxide, and generally over 97%.

Briefly stated, the present invention comprises a process for the concentration of ethylene oxide in an impure solution thereof comprising adding said solution and steam to a distillation column, recovering the gaseous stream therefrom containing ethylene oxide, and progressively condensing said steamed solution in at least two heat exchangers arranged in series, with the absolute pressure of the distillation column and of the exchangers being between about 1.5 and 6 bars and the temperature of the cooling fluid of the last exchanger being between about 5° C. and a maximum temperature 5° C. below the temperature of condensation of pure ethylene oxide at the pressure used.

The invention also comprises the apparatus system as hereinafter described and claimed.

BRIEF ESCRIPTION OF THE DRAWING

FIG. 1 is a schematic representation of the apparatus system of the present invention for the process of concentrating an aqueous ethylene oxide solution.

DETAILED DESCRIPTION

Figure 1:
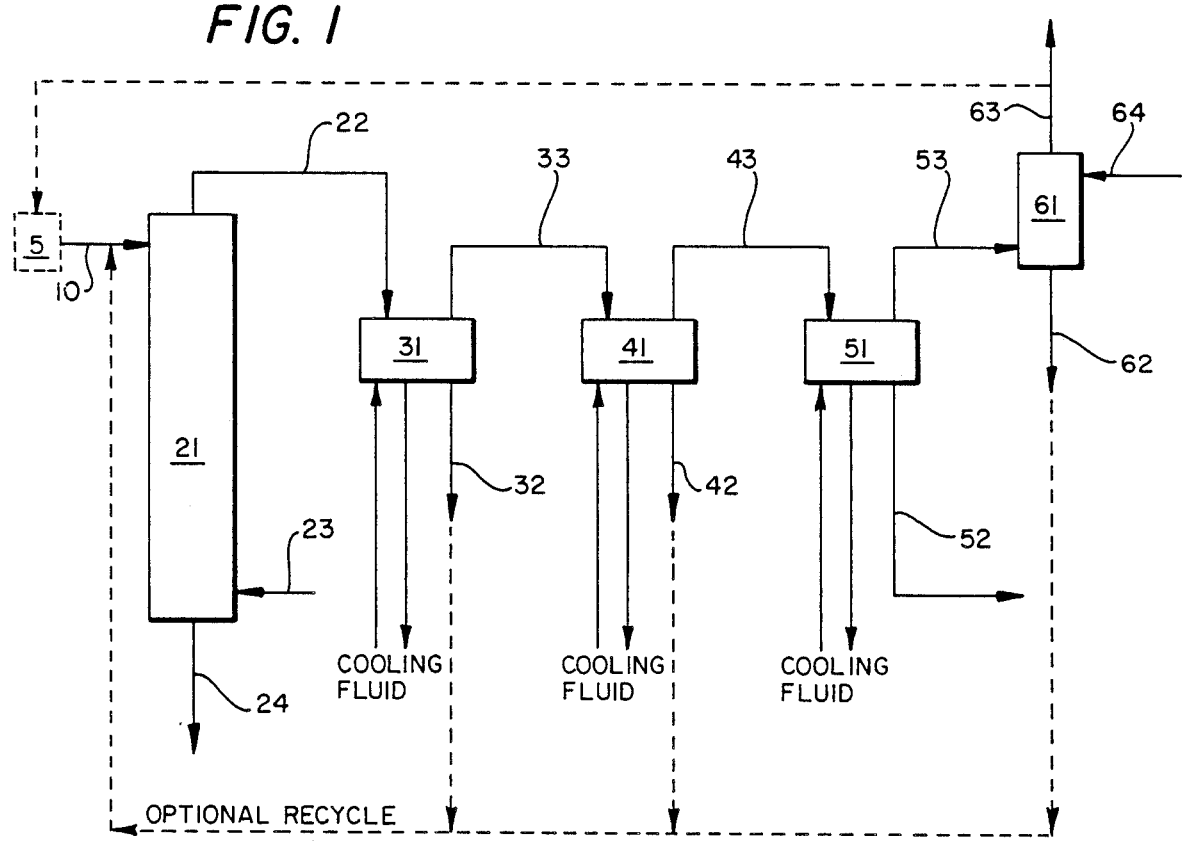

The present invention provides a process and apparatus for progressively condensing the gaseous stream originating from step (b) in two or preferably three heat exchangers arranged in series.

FIG. 1 represents an apparatus system for implementing one preferred process of the invention. This apparatus system comprises basically a distillation column 21, three exchangers 31, 41 and 51, and an absorption column 61.

Column 21 is a conventional distillation column including several theoretical stages or gas-liquid contact devices and can be equipped with an enrichment section. In the upper part of column 21, a very dilute aqueous ethylene oxide solution is introduced as stream 10, and may contain dissolved gases (in general less than 0.25% by weight) and other impurities. At 24, one obtains an aqueous stream without dissolved gases and impurities, and lacking ethylene oxide. At 22, one obtains a mixture of ethylene oxide (about 30 to 60% by weight) and steam as well as the major portion of the dissolved gases and the impurities possibly present in stream 10. The energy of separation is furnished by steam injection 23 at the base of column 21, or by a reheater supplied by any hot source. Column 21 functions in a standard and conventional manner.

Gaseous stream 22 is then condensed in three exchangers arranged in series The first two (31 and 41) allow a partial condensation and the third one (51) a total condensation of the ethylene oxide. At 52, a liquid phase is collected containing over 95% by weight of ethylene oxide, a small amount of water, a small portion of the $CO_2$ dissolved in stream 10 and some impurities (principally formaldehyde and acetaldehyde). At 53, a gaseous phase formed by the major portion of dissolved gases and a small portion of the impurities contained in stream 10 is collected, mixed with oxide vapors and steam. This stream 53 is washed in an absorption column 61, possessing several theoretical stages or gas-liquid contact devices, by a water stream 64 in order to recover at 62 an aqueous ethylene oxide solution and at 63 a portion of the gases dissolved in stream 10.

Column 21, as well as its gas-liquid contact devices and exchangers 31, 41 and 51 are of standard dimensions. The pressure of column 21 and of exchangers 31, 41 and 51 is the same except for pressure loss due to the circulation of the fluids in apparatuses 21, 31, 41 and 51 and their piping. The absolute pressure of the entire apparatus is between 1.5 and 6 bars, advantageously between 1.6 and 4 bars, and more particularly preferably between 1.9 and 3 bars. The temperature of the cold source of exchanger 51 is regulated between 5° C. and at a maximum temperature 5° C. lower than the temperature of condensation of pure ethylene oxide at the pressure under consideration. This cold source can be air according to the climatic conditions of the site of operation of the exchanger, or more often cooling water.

Stream 22, whose temperature generally is between 90 and 150° C., is partially condensed in exchanger 31 in such a way that the liquid phase 32 does not contain more than 12% of the ethylene oxide contained in stream 22. This adjustment is easily obtained by acting on the cold source of exchanger 31. The cold source can, for instance, be cooling water between 10 and 40° C.

Exchanger 41 is used as partial condenser for recovering, in the gaseous phase of outlet 43, the major portion of the ethylene oxide introduced by stream 33, while keeping in this phase 43 an amount of water below 5% in relation to the weight of ethylene oxide. These proportions are adjusted by acting on the cooling fluid of exchanger 41. In order to find the temperature adjustment, one starts condensing at a temperature slightly below that of stream 33. Then, while measuring the amounts of water and of ethylene oxide in phases 42 and 43, this temperature is progressively lowered until obtaining the desired ethylene oxide concentration in gaseous phase 43. The cold source of exchanger 41 can, for instance, be cooling water between 10 and 40° C. Stream 43 is condensed in exchanger 51. At 53, one collects the major portion of gases possibly dissolved in stream 10 and a small part of the impurities of stream 10 mixed with oxide vapors and steam. At 52, one collects almost all of the ethylene oxide of stream 43 (except for the small part possibly carried along in stream 53), water, some impurities and a small part of the $CO_2$ initially dissolved in stream 10.

Stream 52 which contains over 95% by weight of ethylene oxide, and generally over 97%, can be used as is or, depending on its final destination, it can be purified.

Stream 53 is washed in absorption column 61 with water (stream 64) at a temperature between 5° and 50° C. The water can be replaced by an aqueous glycol solution available in the process Column 61 operates in a conventional manner, with the flow rate of stream 64 being selected as a function of the number of theoretical stages or of gas-liquid contact devices of the column In general, stream 53 represents less than 5% by weight, most often less than 1% of stream 10; three to six theoretical stages suffice in order to recover the major portion of the ethylene oxide of stream 53. A gas 63 contains the major portion of the gases dissolved in stream 10 and a small amount of steam. After compression, this gas which contains a significant, proportion of ethylene can be sent back into the reaction zone 5. A liquid 62 is collected consisting of an aqueous ethylene oxide solution which can be mixed with streams 32 and 42. This mixture can be treated thermally in order to make glycol or distilled in order to prepare pure ethylene oxide or even remixed with stream 10 for the production of concentrated ethylene oxide (52). After cooling, stream 24 can be used in order to absorb ethylene oxide (step a) and recycled into column 21 as stream 10.

Exchanger 31 can also be eliminated. In that case, the operation remains the same except for the adjustment of the cold source of exchanger 41. This cold source is adjusted in such a way as to collect the major portion of the ethylene oxide of stream 22 in gas phase 43, but the amount of water in phase 43 must remain below 5% of the weight of ethylene oxide. In order to adjust the temperature of phase 43, the temperature of stream 22 is utilized as the basis rather than that of stream 33.

The invention will be further illustrated in conjunction with the following examples, which are set forth for purposes of illustration only and not by way of limitation.

Tables I to VI summarize the operating conditions and the results obtained in the six examples illustrating the invention. The stream numbers correspond to those of FIG. 1. In addition, trace impurities (such as formaldehyde and acetaldehyde) have not been indicated.

EXAMPLES 1, 2, AND 3

Examples 1, 2 and 3 corresponding respectively to Table I, II and III have been obtained under the same conditions of pressure (2.7 to 2.5 bars) from aqueous ethylene oxide solutions containing decreasing quantities of dissolved gas.

EXAMPLE 4

Example 4 (Table IV) has been obtained from the same aqueous ethylene oxide solution as in Example 1 but by operating at a higher pressure (3.45 to 3.25 bars)

EXAMPLE 5

Example 5 is the same as Example 3 but at a much smaller pressure (2 to 1.8 bars). An examination of the results indicated on Table V shows, in comparison with those of Example 4, that one obtains similar flow rates 52 and 53, although working at a pressure only half as much.

EXAMPLE 6

Example 6 (Table VI) illustrates the use of only two exchangers (41 and 51).

TABLE I

| STREAM NO. | 10 | 22 | 32 | 33 | 42 | 43 | 52 | 53 |
|---|---|---|---|---|---|---|---|---|
| Absolute Pressure ($kg/cm^2$) | 2.7 | 2.7 | 2.6 | 2.6 | 2.54 | 2.54 | 2.5 | 2.5 |
| Temperature (°C.) | 108 | 114 | 75 | 75 | 42 | 42 | 25 | 25 |
| Flow Rate (kg/h) | 1900 | 88.54 | 36.54 | 52 | 4.36 | 47.6 | 34.2 | 13.4 |
| Composition (% By Weight) | | | | | | | | |
| Ethylene Oxide | ≈2.6 | 54.67 | 11.14 | 85.26 | 35.29 | 89.84 | 97.47 | 70.3 |
| Water | ≈92 | 40.43 | 88.71 | 6.51 | 64.7 | 1.19 | 1.57 | 0.21 |
| Ethylene Glycol | 5.2 | 0.05 | 0.13 | * | * | * | * | * |
| $CO_2$ | 0.17 | 3.73 | * | 6.34 | 0.013 | 6.9 | 0.79 | 22.6 |
| $C_2H_4$ | 0.032 | 0.69 | * | 1.18 | * | 1.3 | 0.16 | 4.2 |

TABLE I-continued

| STREAM NO. | 10 | 22 | 32 | 33 | 42 | 43 | 52 | 53 |
|---|---|---|---|---|---|---|---|---|
| $N_2$, $CH_4$, Argon ... | 0.019 | 0.43 | * | 0.71 | * | ≈0.77 | 8 | 2.67 |

*Trace Amount

TABLE II

| STREAM NO. | 10 | 22 | 32 | 33 | 42 | 43 | 52 | 53 |
|---|---|---|---|---|---|---|---|---|
| Absolute Pressure ($kg/cm^2$) | 2.7 | 2.7 | 2.6 | 2.6 | 2.54 | 2.54 | 2.5 | 2.5 |
| Temperature (°C.) | 108 | 115 | 75 | 75 | 42 | 42 | 25 | 25 |
| Flow Rate (kg/h) | 1900 | 83.64 | 35 | 48.65 | 4.32 | 44.32 | 41.5 | 2.8 |
| Composition (% By Weight) | | | | | | | | |
| Ethylene Oxide | ≈2.6 | 57.88 | 12.04 | 90.84 | 39.52 | 95.85 | 97.7 | 68.79 |
| Water | 91.9 | 40.47 | 87.8 | 6.42 | 60.46 | 1.15 | 1.22 | 0.17 |
| Ethylene Glycol | 5.43 | 0.06 | 0.13 | * | * | * | * | * |
| $CO_2$ | 0.065 | 1.47 | * | 2.53 | * | 2.77 | 1.01 | 28.43 |
| $C_2H_4$ | 0.003 | 0.067 | 8 | 0.115 | * | 0.12 | 0.05 | 1.26 |
| $N_2$, $CH_4$, Argon ... | 0.002 | 0.048 | * | 0.08 | * | 0.09 | * | 1.34 |

*Trace Amount

TABLE III

| STREAM NO. | 10 | 22 | 32 | 33 | 42 | 43 | 52 | 53 |
|---|---|---|---|---|---|---|---|---|
| Absolute Pressure ($kg/cm^2$) | 2.7 | 2.7 | 2.6 | 2.6 | 2.54 | 2.54 | 2.5 | |
| Temperature (°C.) | 108 | 115 | 75 | 75 | 42 | 42 | 25 | |
| Flow Rate (kg/h) | 1900 | 78.2 | 33.9 | 44.3 | 4.04 | 40.25 | 40.3 | ≈0 |
| Composition (% By Weight) | | | | | | | | |
| Ethylene Oxide | ≈2.5 | 57.97 | 12.31 | 92.93 | 40.9 | 98.15 | 98.15 | |
| Water | 92.25 | 41.61 | 87.55 | 6.43 | 59.1 | 1.15 | 1.15 | |
| Ethylene Glycol | 5.24 | 0.05 | 0.13 | * | * | * | * | |
| $CO_2$ | 0.0016 | 0.039 | * | 0.07 | * | 0.076 | 0.076 | |
| $C_2H_4$ | 0.013 | 0.32 | * | 0.56 | * | 0.62 | 0.62 | |
| $N_2$, $CH_4$, Argon ... | * | * | * | * | * | * | * | |

*Trace Amount

TABLE IV

| STREAM NO. | 10 | 22 | 32 | 33 | 42 | 43 | 52 | 53 |
|---|---|---|---|---|---|---|---|---|
| Absolute Pressure ($kg/cm^2$) | 3.45 | 3.45 | 3.35 | 3.35 | 3.29 | 3.29 | 3.25 | 3.25 |
| Temperature (°C.) | 108 | 119 | 75 | 75 | 42 | 42 | 25 | 25 |
| Flow Rate (kg/h) | 1900 | 79.74 | 29 | 50.72 | 5.33 | 45.4 | 37.36 | 8.04 |
| Composition (% By Weight) | | | | | | | | |
| Ethylene Oxide | ≈2.6 | 60.71 | 15.26 | 86.7 | 60.83 | 89.75 | 97.2 | 55.16 |
| Water | ≈92 | 33.87 | 84.6 | 4.86 | 39.15 | 0.83 | 0.99 | 0.11 |
| Ethylene Glycol | 5.2 | 0.05 | 0.133 | * | * | * | * | * |
| $CO_2$ | 0.17 | 4.13 | * | 6.5 | 0.015 | 7.26 | 1.5 | 34.01 |
| $C_2H_4$ | 0.032 | 0.77 | * | 1.21 | * | 1.35 | 0.296 | 6.27 |
| $N_2$, $CH_4$, Argon ... | 0.019 | 0.45 | * | 0.71 | * | ≈0.8 | * | 4.42 |

*Trace Amount

TABLE V

| STREAM NO. | 10 | 22 | 32 | 33 | 42 | 43 | 52 | 53 |
|---|---|---|---|---|---|---|---|---|
| Absolute Pressure ($kg/cm^2$) | 2 | 2 | 1.9 | 1.9 | 1.84 | 1.84 | 1.8 | 1.8 |
| Temperature (°C.) | 108 | 110 | 75 | 75 | 42 | 42 | 25 | 25 |
| Flow Rate (kg/h) | 1900 | 97.49 | 51.9 | 45.58 | 4.76 | 40.81 | 33.78 | 7.04 |
| Composition (% By Weight) | | | | | | | | |
| Ethylene Oxide | ≈2.5 | 46.5 | 8.23 | 90.1 | 25.72 | 97.6 | 97.9 | 96.15 |
| Water | 92.25 | 53.14 | 91.64 | 9.3 | 74.27 | 1.71 | 1.99 | 0.35 |
| Ethylene Glycol | 5.24 | 0.069 | 0.129 | * | * | * | * | * |
| $CO_2$ | 0.0016 | 0.031 | * | 0.067 | * | 0.075 | 0.01 | 0.39 |
| $C_2H_4$ | 0.013 | 0.25 | * | 0.54 | * | 0.61 | 0.091 | 3.11 |
| $N_2$, $CH_4$, Argon ... | * | * | * | * | * | * | * | * |

*Trace Amount

TABLE VI

| STREAM NO. | 10 | 22 | 32 | 33 | 42 | 43 | 52 | 53 |
|---|---|---|---|---|---|---|---|---|
| Absolute Pressure ($kg/cm^2$) | 2.7 | 2.7 | | | 2.54 | 2.54 | 2.5 | 2.5 |
| Temperature (°C.) | 108 | 115 | | | 42 | 42 | 25 | 25 |

TABLE VI-continued

| STREAM NO. | 10 | 22 | 32 | 33 | 42 | 43 | 52 | 53 |
|---|---|---|---|---|---|---|---|---|
| Flow Rate (kg/h) | 1900 | 83.64 | | | 54.57 | 29.07 | 25.71 | 3.37 |
| Composition (% By Weight) | | | | | | | | |
| Ethylene Oxide | ≃2.6 | 57.88 | | | 38.5 | 94.28 | 97.63 | 68.71 |
| Water | 91.9 | 40.47 | | | 61.41 | 1.16 | 1.28 | 0.17 |
| Ethylene Glycol | 5.43 | 0.057 | | | 0.087 | * | * | * |
| $CO_2$ | 0.064 | 1.47 | | | * | 4.22 | 1.02 | 28.64 |
| $C_2H_4$ | 0.003 | 0.067 | | | * | 0.193 | 0.05 | 1.28 |
| $N_2$, $CH_4$, Argon ... | 0.002 | 0.049 | | | * | 0.14 | | 1.2 |

*Trace Amount

While the invention has been described in connection with a preferred embodiment, it is not intended to limit the scope of the invention to the particular form set forth, but, on the contrary, it is intended to cover such alternatives modifications and equivalents as may be included within the spirit and scope of the invention as defined by the appended claims

What is claimed is:

1. A process for the concentration of ethylene oxide present in an aqueous solution obtained by water absorption of ethylene oxide in order to separate it from a gaseous mixture produced during the catalytic oxidation in the gaseous phase of ethylene by oxygen, consisting essentially of the steps of adding said solution and steam to a distillation column so as to recover at the base of said column an aqueous stream free of ethylene oxide and at the top a gaseous stream containing ethylene oxide, progressively condensing said gaseous stream in three heat exchangers arranged in series, recovering from each exchanger a liquid phase and a gaseous stream which gaseous stream successively circulates through each of the exchangers with the absolute pressure of the distillation column and of the exchangers being between about 1.5 and 6 bars, washing only the gaseous stream recovered from the last heat exchanger in said series by an aqueous stream in an absorption column, adjusting the temperature of the cooling fluid of the first and the second heat exchangers such that the liquid phase emerging from the first exchanger does not contain over 12% of the ethylene oxide contained in the gaseous stream entering said exchangers and that the proportion of water contained in the gaseous stream leaving the second exchanger is below 5% in relation to the weight of ethylene oxide, and the temperature of the cooling fluid of the last exchanger is between about 5° C. and a maximum temperature 5° C. below the temperature of condensation of pure ethylene oxide at the pressure used, and recovering the liquid phase from the last exchanger which contains over 95% by weight of ethylene oxide.

2. The process of claim 1 wherein the liquid phases from the exchangers are recycled with the ethylene oxide solution entering into the distillation column.

3. The process of claim 1, wherein the gaseous stream from the last exchanger is absorbed by water or an aqueous glycol solution.

4. The process according to claim 3, wherein the gaseous stream resulting from the absorption following the last exchanger is recycled into a reaction zone.

5. The process of claims 1, 2, 3 or 4 wherein the absolute pressure of the distillation column and of the exchangers in series is between 1.6 and 4 bars.

6. A process for the concentration of ethylene oxide present in an aqueous solution obtained by water absorption of ethylene oxide in order to separate it from a gaseous mixture produced during the catalytic oxidation in the gaseous phase of ethylene by oxygen, consisting essentially of the steps of adding said solution and steam to a distillation column so as to recover at the base of said column an aqueous stream free of ethylene oxide and at the top a gaseous stream containing ethylene oxide, progressively condensing said gaseous stream in at least two heat exchangers arranged in series, recovering from each exchanger a liquid phase and a gaseous stream which gaseous stream successively circulates through each of the exchangers with the absolute pressure of the distillation column and of the exchangers being between about 1.5 and 6 bars, washing only the gaseous stream recovered from the last heat exchanger in said series by an aqueous stream in an absorption column, wherein the gaseous stream washed in the absorption column contains the ethylene oxide entering said absorption column and represents less than 5% by weight of the aqueous solution of ethylene oxide entering into the distillation column, being carried out by using two heat exchangers, adjusting the temperature of the cooling fluid of the first exchanger such that the proportion of water contained in the gaseous stream leaving said first exchanger is below 5% in relation to the weight of ethylene oxide and that said gaseous stream contains more than 50% of the ethylene oxide contained in the gaseous stream entering said first exchanger, and the temperature of the cooling fluid of the second and last exchanger being between about 5° C. and a maximum temperature 5° C. below the temperature of condensation of pure ethylene oxide at the pressure used, and recovering the liquid phase from the last exchanger which contains over 95% by weight of ethylene oxide.

7. The process of claim 6, wherein the liquid phase from the exchangers are recycled with the ethylene oxide solution entering into the distillation column.

8. The process of claim 6, wherein the gaseous stream from the last exchanger is absorbed by water or an aqueous glycol solution.

9. The process according to claim 8, wherein the gaseous stream resulting from the absorption following the last exchanger is recycled into a reaction zone.

10. The process of claims 6, 7, 8, or 9 wherein the absolute pressure of the distillation column and of the exchangers in series is between 1.67 and 4 bars.

11. The process of claim 7, wherein the liquid phases from the absorption following the last exchanger are recycled with ethylene oxide solution entering into the distillation column.

* * * * *

UNITED STATES PATENT AND TRADEMARK OFFICE
CERTIFICATE OF CORRECTION

PATENT NO. : 4,983,260
DATED : January 8, 1991
INVENTOR(S) : Neel, et al

It is certified that error appears in the above-identified patent and that said Letters Patent is hereby corrected as shown below:

Col. 7, line 41, after "column," insert
-- wherein the gaseous stream washed in the absorption column contains the ethylene oxide entering said absorption column and represents less than 5% by weight of the aqueous solution of ethylene oxide entering into the distillation column, --; and Col. 8, line 61, delete "1.67" and substitute therefor -- 1.6 --.

Signed and Sealed this

Twenty-third Day of June, 1992

Attest:

DOUGLAS B. COMER

*Attesting Officer*  *Acting Commissioner of Patents and Trademarks*